(12) United States Patent
Rihn

(10) Patent No.: US 12,708,528 B2
(45) Date of Patent: Aug. 18, 2026

(54) MULTI-PRONGED AWL FOR INTERVERTEBRAL BODY SPACE

(71) Applicant: Jeffrey Rihn, Wayne, PA (US)

(72) Inventor: Jeffrey Rihn, Wayne, PA (US)

( * ) Notice: Subject to any disclaimer, the term of this patent is extended or adjusted under 35 U.S.C. 154(b) by 37 days.

(21) Appl. No.: 18/763,570

(22) Filed: Jul. 3, 2024

(65) Prior Publication Data

US 2026/0007527 A1 Jan. 8, 2026

(51) Int. Cl.
*A61F 2/46* (2006.01)
*A61F 2/44* (2006.01)

(52) U.S. Cl.
CPC ............ *A61F 2/4611* (2013.01); *A61F 2/447* (2013.01); *A61F 2002/4625* (2013.01)

(58) Field of Classification Search
CPC .......... A61F 2/4611; A61F 2/447; A61F 2/44; A61F 2/442; A61F 2002/4625
USPC .................. 623/17.11–17.16; 606/79–85, 99
See application file for complete search history.

(56) References Cited

U.S. PATENT DOCUMENTS

2010/0152791 A1* 6/2010 Smith ................ A61B 17/1671 606/86 A
2013/0150969 A1* 6/2013 Zipnick ................. A61F 2/4425 623/17.16
2015/0045893 A1* 2/2015 Dinville .................. A61F 2/447 623/17.16
2018/0028329 A1* 2/2018 Suh ....................... A61F 2/4455
2019/0358055 A1* 11/2019 Arnold .................. A61F 2/4465
2022/0331124 A1* 10/2022 Hodrinsky ........... A61B 6/5211
2024/0016503 A1* 1/2024 Nozawa ............. A61B 17/1671

FOREIGN PATENT DOCUMENTS

CN 110251195 A * 9/2019 ......... A61B 17/1604

* cited by examiner

*Primary Examiner* — Jessica Weiss
(74) *Attorney, Agent, or Firm* — McNees Wallace & Nurick LLC

(57) ABSTRACT

A multi-pronged awl includes a shaft, a handle extending from a first end of the shaft, and a head extending from the shaft at a second end of the shaft opposite the first end. The head includes a housing and prongs mounted in a cavity of the housing. Activation of the handle portion moves the plurality of prongs between a retracted state within the housing and an extended state extending past an edge on a first side of the housing. A method of repairing a damaged disc space between two neighboring vertebrae defining the damaged disc space includes actuating a handle of thee multi-pronged awl to move the prongs from the retracted state to the extended state to contact and penetrate a predetermined distance into the endplate of the first vertebra while a back surface of the head presses against the endplate of the second vertebra.

13 Claims, 7 Drawing Sheets

MULTI-PRONGED AWL FOR INTERVERTEBRAL BODY SPACE

FIELD

The present disclosure is generally directed to methods and devices for stabilizing the spinal column. More specifically, the present disclosure is directed to a multi-pronged awl and its use in the intervertebral body space.

DESCRIPTION OF THE RELATED ART

As humans age or as a result of injury, the intervertebral body space or disc space between a pair of endplates of neighboring vertebrae may become damaged or otherwise compromised and require surgery to repair. Such surgery may include removing damaged material in the intervertebral body space and inserting an implant into the intervertebral body space to stabilize the spinal column.

In many cases, the goal of surgery to repair the intervertebral body space is to fuse the two vertebrae together, but this limits the mobility of the spine. In other cases, the goal is to replace the disc with an intervertebral implant. Regardless, the success of the surgery relies on the ability to access and prepare the damaged intervertebral body space and the ability of the body to heal post-surgery.

Conventional preparation of a vertebral endplate for ensuing fusion can require difficult maneuvering and gesturing of surgical instruments, such as curettes or scrapers, to cut or penetrate the bony material of the endplate. Sufficient time and effort during the surgery must be devoted to the use such instruments to obtain the desired result.

U.S. Pat. No. 7,674,265 discloses an instrument that prepares vertebral endplates using pyramidally shaped spikes having a sharpened outer end to penetrate, crush, or otherwise form openings in the bony material of the vertebral endplates of adjacent vertebrae when deployed to promote bleeding of the vertebral endplates and facilitate bone growth and implant incorporation in interbody fusion procedures.

SUMMARY

A multi-pronged awl includes a shaft portion, a handle portion extending from a first end of the shaft portion, and a head portion extending from the shaft portion at a second end of the shaft portion opposite the first end. The head portion includes a housing and a plurality of prongs mounted in a cavity of the housing. Activation of the handle portion moves the plurality of prongs between a retracted state within the housing and an extended state extending past an edge on a first side of the housing.

A method of repairing a damaged disc space between a first vertebra and a second vertebra neighboring the first vertebra, the first vertebra and the second vertebra defining the damaged disc space, includes actuating a handle of a multi-pronged awl to move a plurality of prongs from a retracted state within a cavity in a head of the multi-pronged awl to an extended state extending past an edge of the cavity to contact and penetrate a predetermined distance into a first endplate of the first vertebra while a back surface of the head presses against a second endplate of the second vertebra.

Various features and advantages of the present invention will be apparent from the following more detailed description, taken in conjunction with the accompanying drawings which illustrate, by way of example, the principles of the invention.

BRIEF DESCRIPTION OF THE DRAWINGS

Wherever possible, the same reference numbers will be used throughout the drawings to represent the same parts.

DETAILED DESCRIPTION

Figures 1, 2:
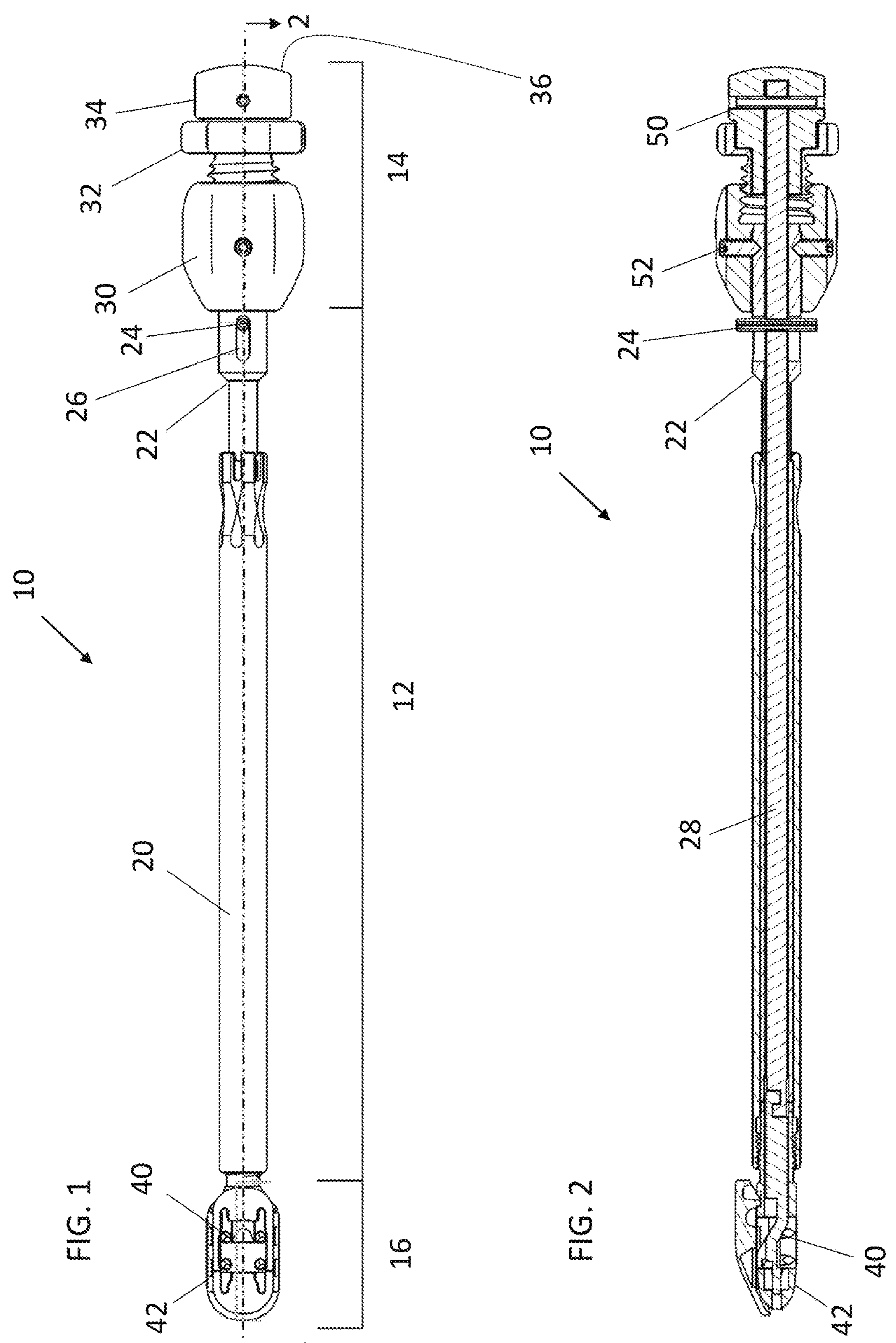
FIG. 1 shows a top view of a multi-pronged awl with the prongs in a retracted state in an embodiment of the present disclosure.
FIG. 2 shows a partial cross-sectional side view of the awl of FIG. 1 along line 2-2.

The general inventive concepts will now be described with occasional reference to the exemplary embodiments. The general inventive concepts may be embodied in different forms and should not be construed as limited to the embodiments set forth herein. Rather, these embodiments are provided so that this disclosure will be thorough and complete, and will fully convey the scope of the general inventive concepts to those skilled in the art.

As used herein, the singular forms "a," "an," and "the" are intended to include the plural forms as well, unless the context clearly indicates otherwise. The term "proximal" as used in connection with any object refers to the portion of the object that is closest to the operator of the object (or some other stated reference point), and the term "distal" refers to the portion of the object that is farthest from the operator of the object (or some other stated reference point). The term "operator" means and refers to any professional or paraprofessional who delivers clinical care to a medical patient, particularly in connection with the delivery of care.

Anatomical references as used herein are intended to have the standard meaning for such terms as understood in the medical community. For example, the application may include reference to the following terms: "dorsal" and "posterior" indicate a direction toward the back, and "ventral" and "anterior" indicate a direction toward the front. The term "lateral" indicates a direction toward a side of the patient. The term "medial" indicates a direction toward the mid line of the patient, and away from the side, the term "ipsilateral" indicates a direction toward a side that is proximal to the operator or the object being referenced, and the term "contralateral" indicates a direction toward a side that is distal to the operator or the object being referenced. And, more specifically with respect to the directional movement of an implant according to the methods of the disclosure, sideways refers to the general direction of movement within the disc space between the endplates from the position of the inserted instruments toward one or the other of the contralateral and ipsilateral portions of the disc space. In the case of a procedure, such sideways motion will generally be in a medial direction relative to the disc space. Though in other types of surgical access, particularly within the spine, sideways movement may be either medial or lateral relative to the disc space, and in other surgical contexts sideways is away from the initial position of the implant. Further, with respect to the movement of an implant by action of the surgical instruments, the movement may also be rotational, wherein the action of the instruments directs the implant sideways and also in a rotational or pivotal motion. More generally, any and all terms providing spatial references to anatomical features shall have meaning that is customary in the art.

Unless otherwise indicated, all numbers expressing quantities, properties, and so forth as used in the specification, drawings and claims are to be understood as being modified in all instances by the term "about." Accordingly, unless otherwise indicated, the numerical properties set forth in the specification and claims are approximations that may vary depending on the suitable properties desired in embodiments of the present invention. Notwithstanding that the numerical ranges and parameters setting forth the broad scope of the general inventive concepts are approximations, the numerical values set forth in the specific examples are reported as precisely as possible. Any numerical values, however, inherently contain certain errors necessarily resulting from error found in their respective measurements.

References to visualization using radiography as may be described in the exemplary techniques herein are merely representative of the options for the operator to visualize the surgical field and the patient in one of many available modalities. It will be understood by one of ordinary skill in the art that alternate devices and alternate modalities of visualization may be employed depending on the availability in the operating room, the preferences of the operator and other factors relating to exposure limits. While confirmation of instrument placement in the course of the technique is appropriate, the frequency and timing relative to the sequence of steps in the technique may be varied and the description herein is not intended to be limiting. Accordingly, more or fewer images, from more or fewer perspectives, may be collected.

One of ordinary skill will appreciate that references to positions in the body are merely representative for a particular surgical approach. Further, all references herein are made in the context of the representative images shown in the drawings. Fewer or additional instruments, including generic instruments, may be used according to the preference of the operator. Moreover, references herein to specific instruments are not intended to be limiting in terms of the options for use of other instruments where generic options are available, or according to the preference of the operator.

A multi-pronged awl penetrates the endplate of a vertebra to a depth that allows bone marrow to leak out into the disc space to facilitate bone growth during a healing period post-surgery, which avoids the need to prepare the endplate by removing tissue and exposing the bleeding bony endplate.

In exemplary embodiments, the awl penetrates the endplate to a depth that allows access to the bone marrow of the vertebrae, allowing the bone marrow to fill the intervertebral body space and facilitate the fusion. In exemplary embodiments, the awl does not crush the endplate, but rather penetrates it. Crushing the endplate can lead to cage subsidence. Rather, the awl penetrates the endplate in a controlled fashion without crushing it and while maintaining its structural integrity.

Referring to FIG. 1, a multi-pronged awl 10 includes a shaft portion 12, a handle portion 14 at a first end of the shaft portion 12, and a head portion 16 at a second end of the shaft portion opposition the first end.

The shaft portion 12 of the awl 10 includes an outer retainer shaft 20 and a midshaft 22 extending through the hollow bore of the retainer shaft 20. The midshaft 22 is sized to locate the handle portion 14 an appropriate distance away from the head portion 16 when the head portion is at a location of use, such as, for example, an intervertebral body space. The handle portion 14 of the awl 10 includes a handle knob 30, a retraction knob 32 threaded at a first end and received in a threaded first end of the handle knob 30, and a deployment collar 34 extending at a first end into the second end of the retraction knob 32 and having a striker face 36 at a second end of the deployment collar 34. The handle knob 30 and retraction knob 32 are sized and shaped for convenient manipulation by the user of the awl 10. The striker face 36 may receive a strike from a mallet to aid in driving the head portion 15 of the awl 10 into an appropriate worksite.

A position pin 24 in a slot 26 of the midshaft 22 limits rotational actuation of the retraction knob 32 with respect to the handle knob 30 and indicates the position of the prongs 40 of the head portion 16 of the multi-pronged awl 10. With the position pin 24 in the position shown in FIG. 1, the prongs 40 are retracted below the edge of the housing 42 of the head portion 16 of the awl 10.

Referring to FIG. 2, the shaft portion 12 of the awl 10 also includes an activation shaft 28 extending from the hollow bore of the midshaft 22, through the hollow bores of the handle knob 30 and retraction knob 32 and into the hollow bore of the deployment collar 34, where it is held in place by a spring pin 50 perpendicular to the central axis of the awl 10. The position pin 24 extends perpendicular to the central axis of the awl 10 through the midshaft 22 and the activation shaft 28. The midshaft 22 is retained in the handle portion 14 by a pair of set screws 52 extending from a bore in the handle knob 30 and into the midshaft 22.

Figures 3, 4:
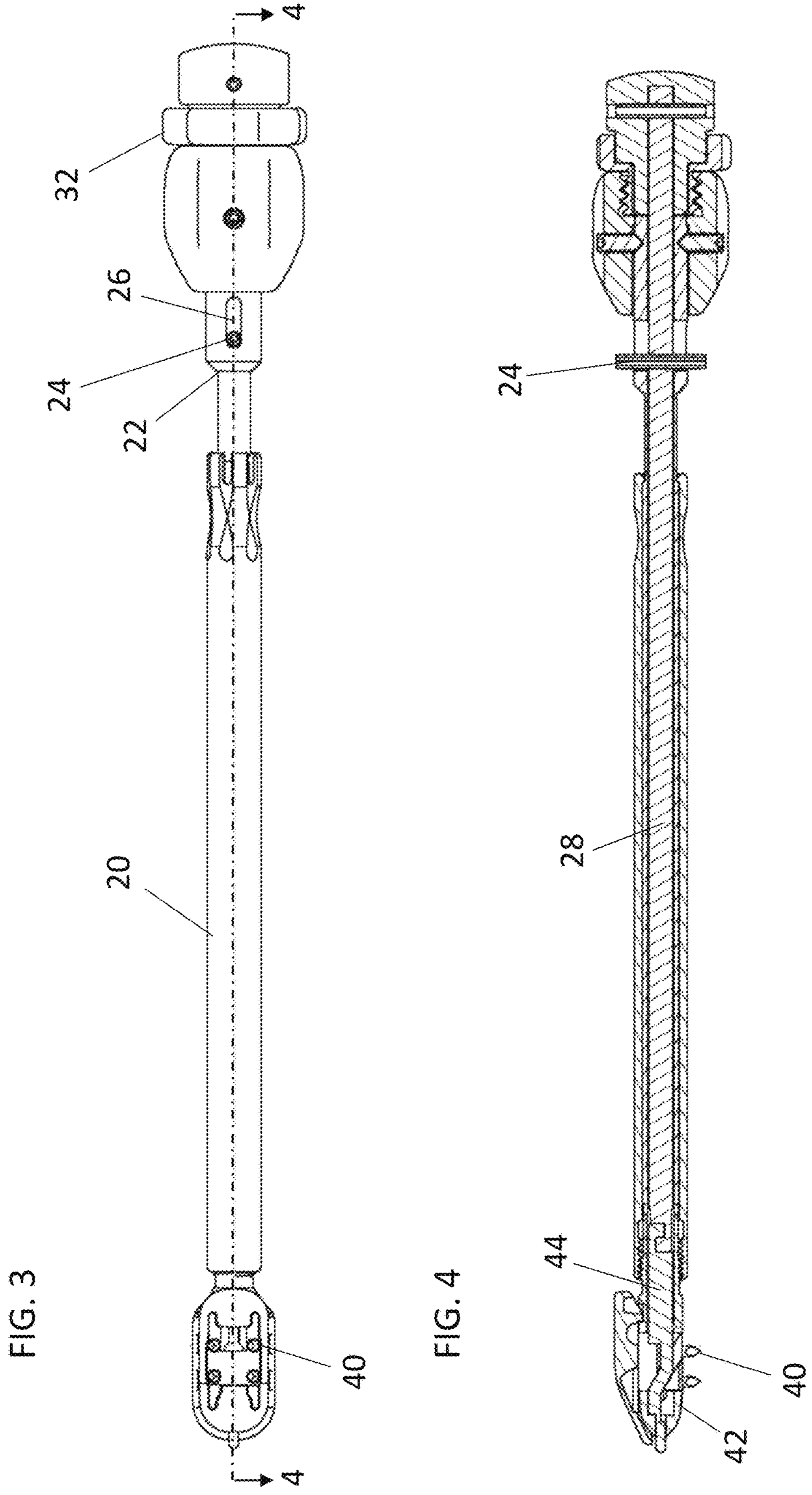
FIG. 3 shows a top view of the multi-pronged awl of FIG. 1 with the prongs in an extended state.
FIG. 4 shows a partial cross-sectional side view of the awl of FIG. 3 along line 4-4.

Referring to FIG. 3 and FIG. 4, the awl 10 is actuated to extend the prongs 40 by rotating the retraction knob 32 in a first direction around the central axis of the awl 10, which drives the activation shaft 28 within the midshaft 22 along the central axis of the awl 10 toward the head portion of the awl 10. This drives a deployment shaft 44 at the end of the activation shaft 28 toward the distal end of the head portion 16, which pushes the prongs 40 perpendicularly away from the central axis of the awl 10 to extend past the edge of the housing 42 of the head portion 16. Additionally, the position pin 24 slides from one end of the slot 26 to the other end as the activation shaft 28 slides with respect to the midshaft 22.

Figure 5:
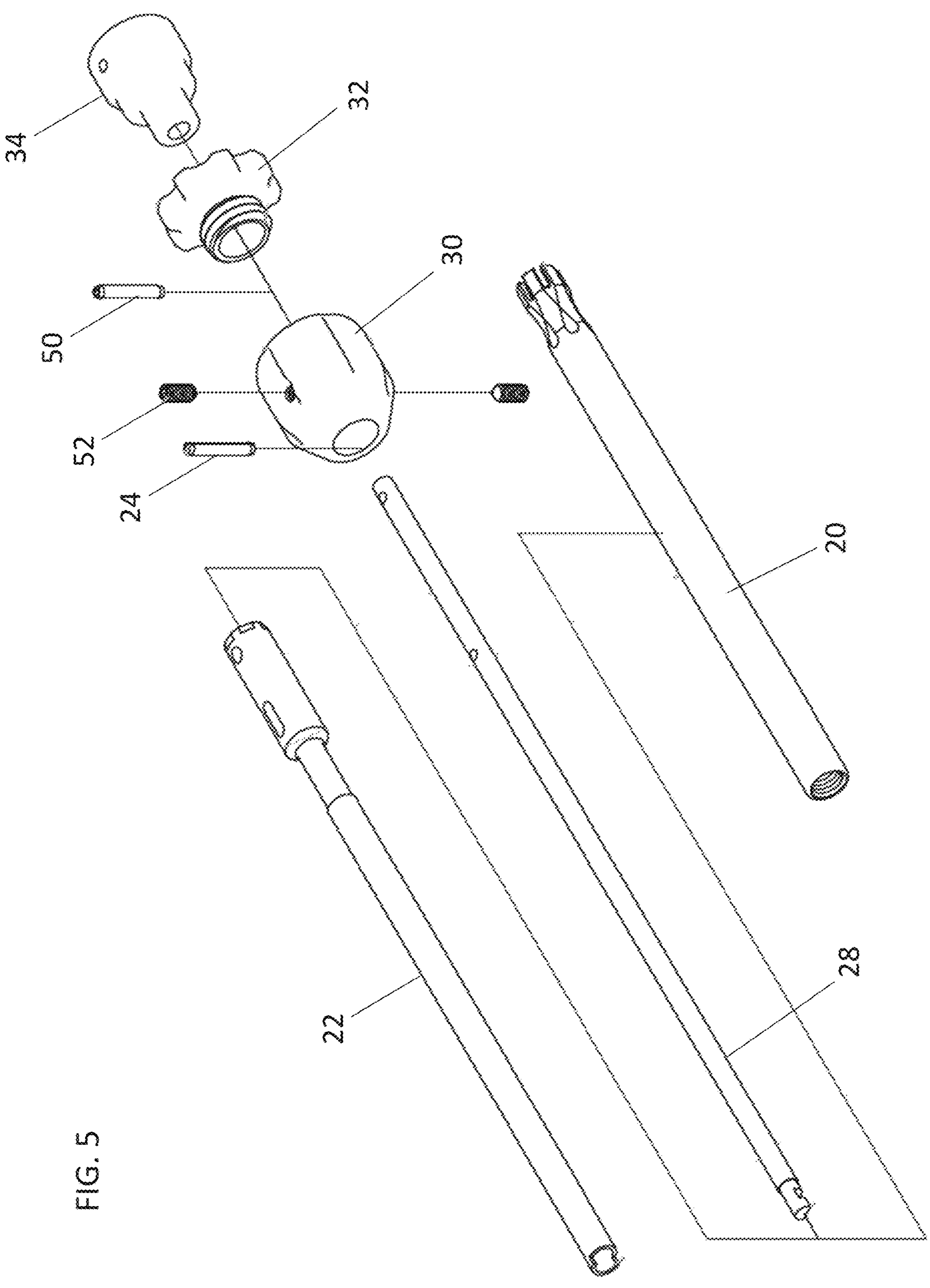
FIG. 5 shows an exploded view of the shaft and handle portions of the awl of FIG. 1.

FIG. 5 shows an exploded view of the components of the shaft portion 12 and the handle portion 14 of the awl 10. The shaft portion 12 includes the retainer shaft 20, the midshaft 22, the activation shaft 28, and the position pin 24. The handle portion 14 includes the handle knob 30, the retraction knob 32, the deployment collar 34, the spring pin 50, and the set screws 52.

Figure 6:
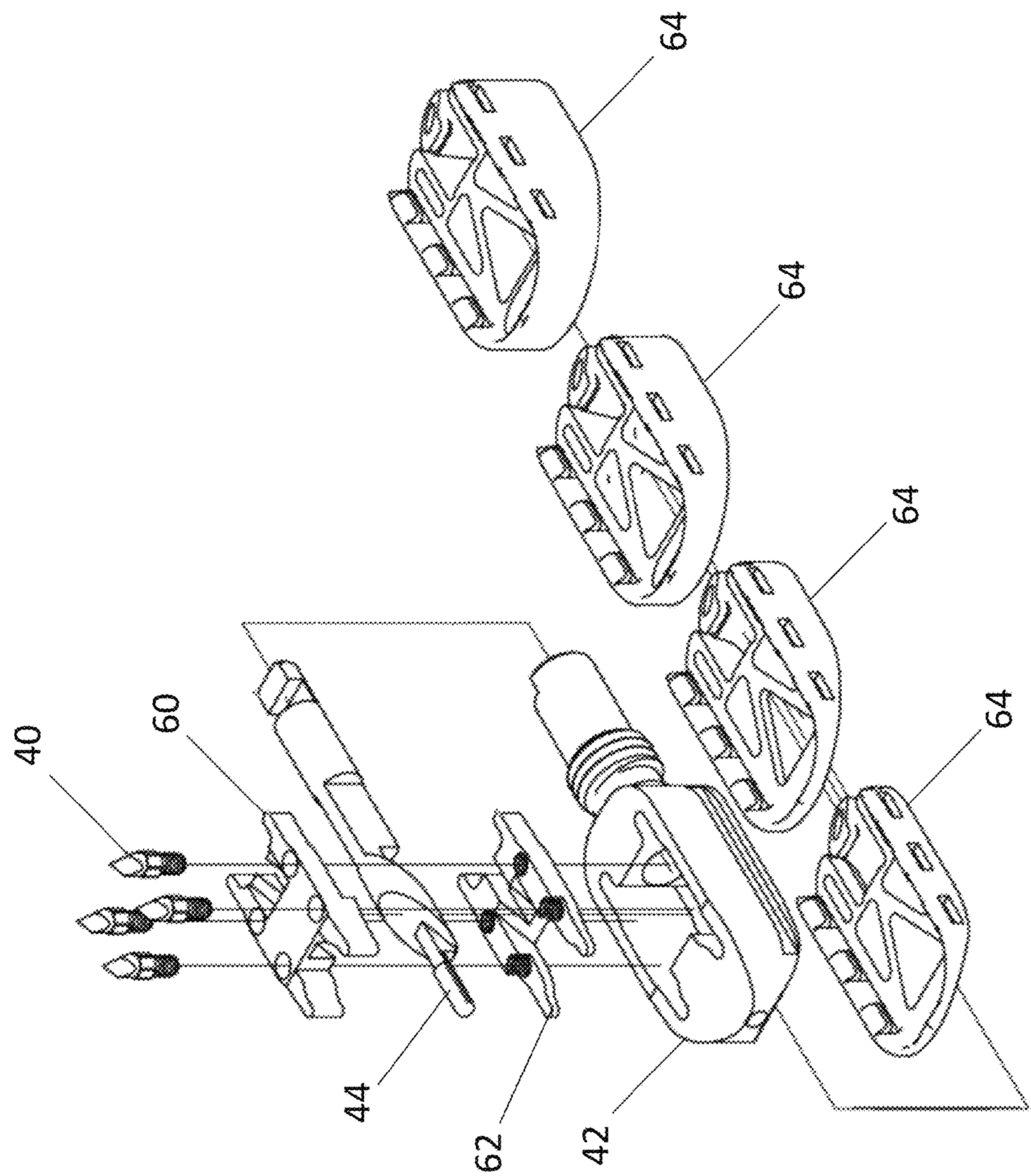
FIG. 6 shows an exploded top view of the head portion of the awl of FIG. 1.

FIG. 6 shows an exploded top view of the components of the head portion 16. The components include the housing 42, which includes a threaded portion that is received in the distal end of the retainer shaft 20. The deployment shaft 44 is received in bore end of the housing 42. A distal tip of the deployment shaft 44 extends into a cavity of the housing 42 between the first trolley half 60 and second the second trolley half 62. The prongs 40 screw into threaded bores in the first trolley half 60. A shim insert 64 is removably affixed to the housing 42 by way of rails on the housing 42 such that the shim insert 64 forms a bottom side of the head portion 16 opposite the top side from which the prongs 40 protrude. Shim inserts 64 of four different sizes are shown in FIG. 6 to provide options of various heights of the head portion 16 of the awl 10.

Figure 7:
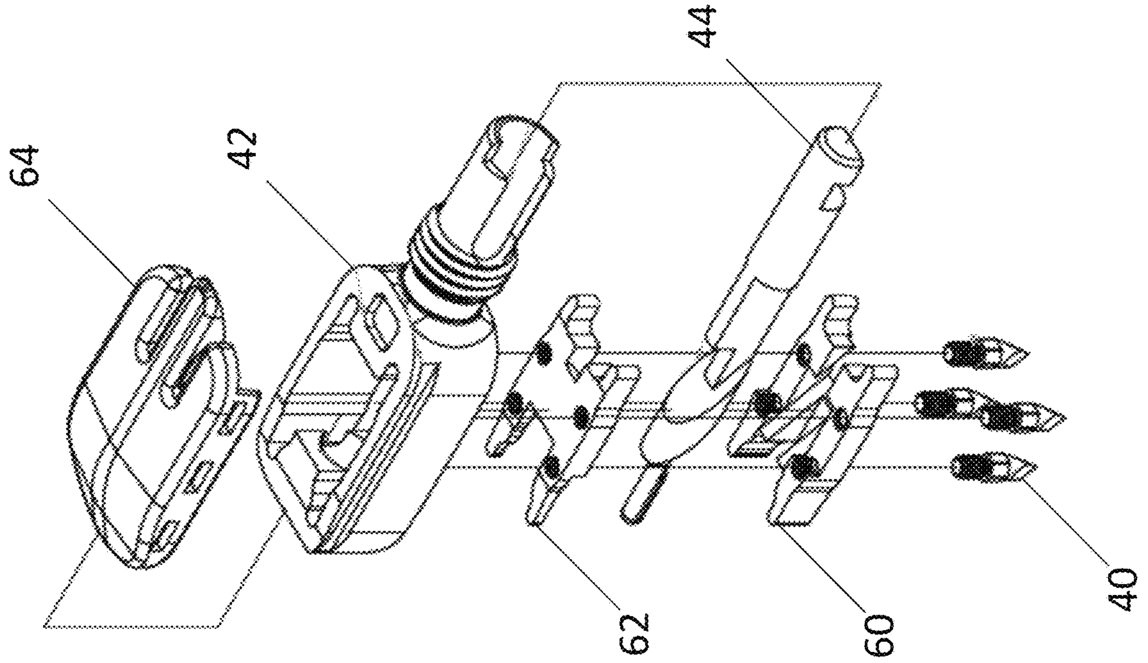
FIG. 7 shows an exploded bottom view of the head portion of the awl of FIG. 1.

FIG. 7 shows an exploded bottom view of the components of the head portion 16, including the prongs 40, the housing 42, the deployment shaft 44, the first trolley half 60, the second trolley half 62, and the shim insert 64.

Upon actuation of the retraction knob 32 from a retracted state to an extended state, the retraction knob 32 drives the deployment collar 34 and hence the activation shaft 28 along the central axis toward the distal head portion 16 of the awl 10. This also drives the deployment shaft 44 at the end of the activation shaft 28 toward the distal end of the head portion 16. A ramped portion of the deployment shaft 44 pushes on a ramped portion of the first trolley half 60, thereby pushing the first trolley half 60 away from the second trolley half 62 in a direction perpendicular to the central axis of the awl 10 and raising the prongs 40 away from the central axis to extend past the housing 42.

Upon actuation of the retraction knob 32 from an extended state to a retracted state, the retraction knob 32 drives the deployment collar 34 and hence the activation shaft 28 along the central axis away from the distal head portion 16 of the awl 10. This also drives the deployment shaft 44 at the end of the activation shaft 28 away from the distal end of the head portion 16. A ramped portion of the deployment shaft 44 pulls away from a ramped portion of the first trolley half 60, thereby permitting the first trolley half 60 to move toward the second trolley half 62 in a direction perpendicular to the central axis of the awl 10 and lowering the prongs 40 toward the central axis to retract into the housing 42. In some embodiments, the first trolley half 60 is biased toward the second trolley half 62, such as, for example, by a spring, to retract the prongs 40 upon retraction of the deployment shaft 44.

Although a specific actuation mechanism is shown in the awl of FIG. 1 through FIG. 7, alternative actuation mechanisms may be employed. Appropriate alternative actuation mechanisms may include, but are not limited to, a toggle switch in the handle portion and a cam system in the head portion.

Although four prongs are shown in the awl of FIG. 1 through FIG. 7, the awl may include any appropriate number of prongs, including, but not limited to, 2, 3, 4, 5, 6, 7, 8, 9, 10, 11, or 12 or more prongs. The prongs are preferably arranged to contact the vertebral endplate substantially with the same amount of force.

Although prongs extend from only one side of the head portion in the awl of FIG. 1 through FIG. 7, the head portion may alternatively include prongs extending from both sides of the head portion. In some embodiments, the activation mechanism simultaneously extends and retracts the prongs on both sides of the head portion. In other embodiments, the activation mechanism selectively extends only the prongs on the first side or only the prongs on the second side at one time. Such embodiments permit penetration of both endplates of an intervertebral body space without removing the awl from the intervertebral body space and reinserting it.

The component of the multi-pronged awl may be made of any materials having the appropriate physical properties to perform their intended function. In some embodiments, the pins and screws are made of stainless steel. In some embodiments, the shim inserts are made of plastic. In some embodiments, the structural components of the multi-pronged awl, which may include, but are not limited to, the outer retainer shaft 20, the midshaft 22, the activation shaft 28, the handle knob 30, the retraction knob 32, the deployment collar 34, and the housing 42, are made of plastic or metal. Appropriate metals may include, but are not limited to, stainless steel, titanium, cobalt chrome, or aluminum.

In exemplary embodiments, the head of the multi-pronged awl is sized and contoured to fit a specific surgical site in the intervertebral body space between two vertebrae of a specific patient. The size and contour of the intervertebral body space and the thickness of the vertebral endplates varies with age and among individuals and among the intervertebral body spaces of an individual (see, for example, Wang et al., "The osseous endplates in lumbar vertebrae: thickness, bone mineral density and their associations with age and disk degeneration", *Bone*, Vol. 48, pp. 804-809, 2011; Pitzen et al., "Variation of endplate thickness in the cervical spine", *Eur. Spine J.*, Vol. 13, pp. 235-240, 2024; and Wang et al., "A morphological study of lumbar vertebral endplates: radiographic, visual and digital measurements", *Eur. Spine J.*, Vol 21, pp. 2316-2323, 2012). In some embodiments, the size and contour of the surgical site and the thickness of the vertebral shell and endplate defining the intervertebral body space are determined by one or more imaging devices or methods. Appropriate imaging methods may include, but are not limited to, computed tomography (CT) (see, for example, Silva et al., "Direct and computed tomography thickness measurement of the human, lumbar vertebral shell and endplate", *Bone*, Vol. 15, pp. 409-414, 1994) and digital tomosynthesis (DTS) (see, for example, Yeni et al., "Measuring the thickness of vertebral endplate and shell using digital tomosynthesis", *Bone*, Vol. 157, 116341, 2022).

Figure 8:
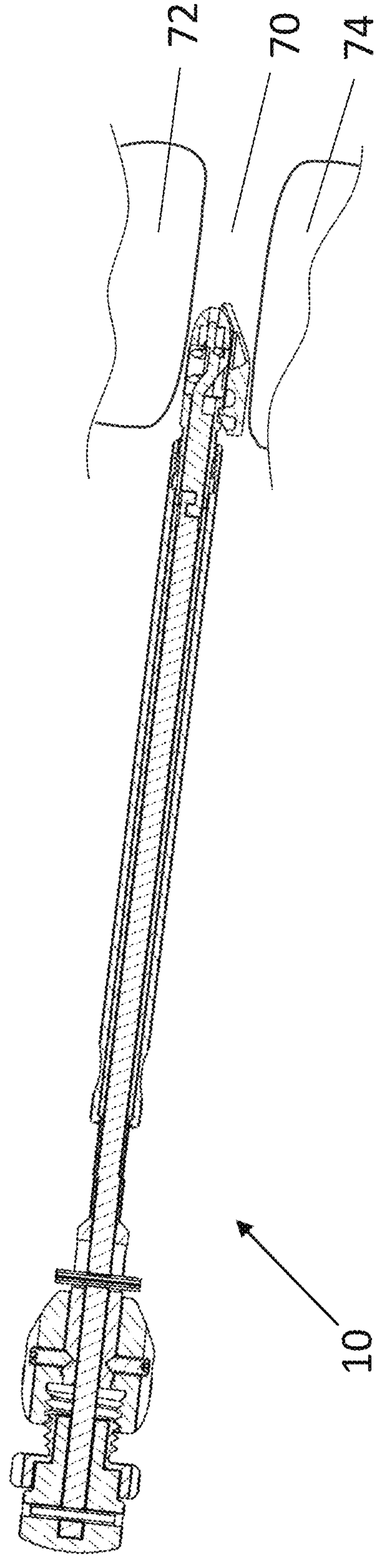
FIG. 8 shows an image of a multi-pronged awl of FIG. 1 being inserted into an intervertebral space.
Figure 9A:
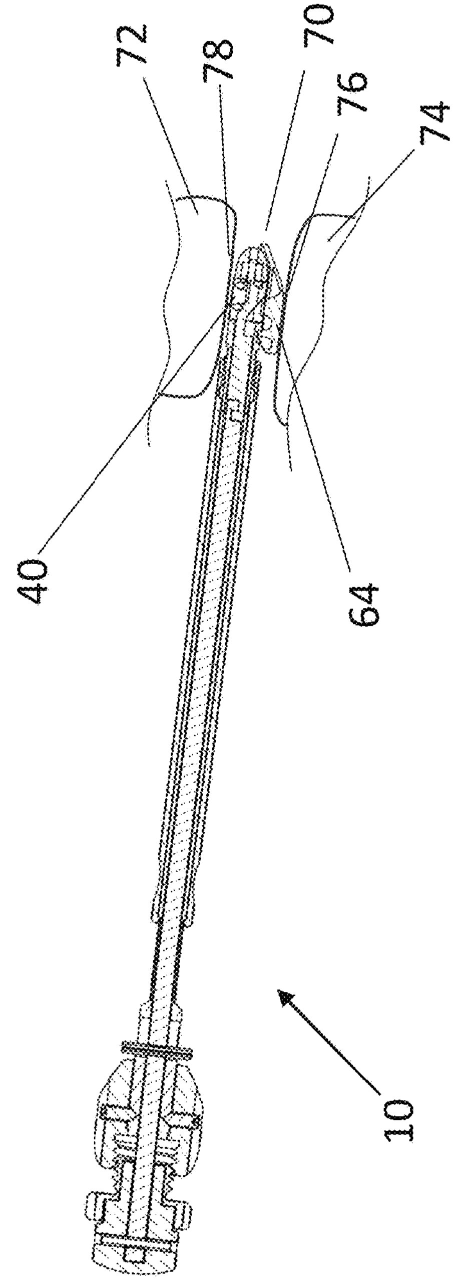
FIG. 9A shows a cross sectional image of the multi-pronged awl of FIG. 8 in the intervertebral space prior to actuation.
Figure 9B:
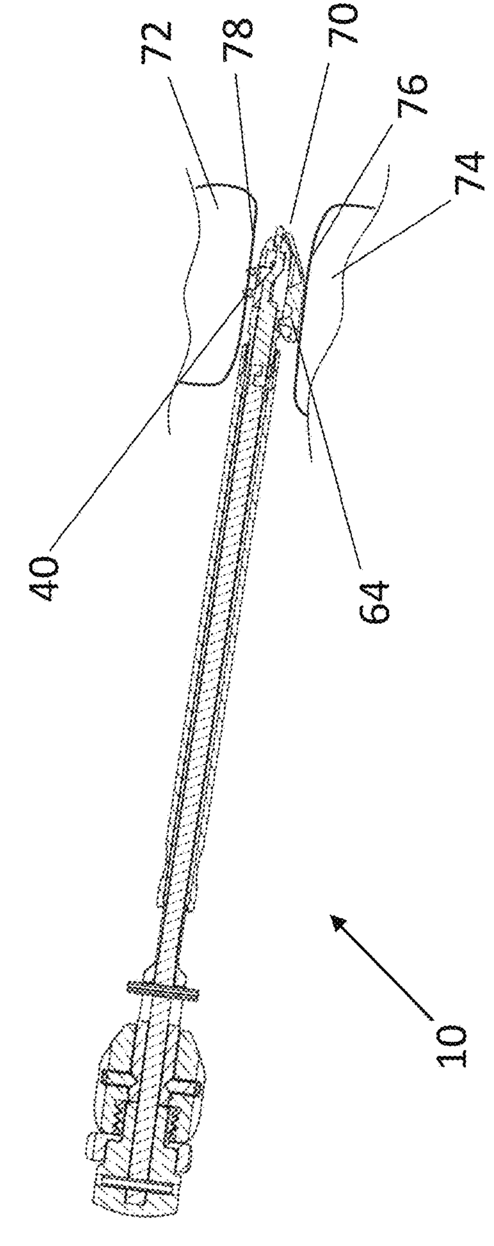
FIG. 9B shows a cross sectional image of the multi-pronged awl of FIG. 9A in the intervertebral space after to actuation.

Referring to FIG. 8, the multi-pronged awl 10 is inserted into a damaged disc space 70 between two vertebrae 72, 74 during a spinal surgery after preparation of the surgical space to remove unwanted material from the damaged disc space 70 and prior to insertion of any implants into the intervertebral body space. FIG. 9A shows the multi-pronged awl 10 in position in the damaged disc space 70 in a retracted state with the shim insert 64 positioned to contact the endplate 76 of the second vertebra 74 and the prongs 40 pointed toward the endplate 78 of the first vertebra 72. Referring to FIG. 9B, an operator actuates the multi-pronged awl 10 to penetrate the endplate 78 of the first vertebra 72 with the prongs 40 of the multi-pronged awl 10 to a depth that allows bone marrow to leak out into the damaged disc space 70 to facilitate bone growth during a healing period post-surgery. The multi-pronged awl 10 is then retracted and withdrawn from the damaged disc space 70. The multi-pronged awl 10 may then be re-inserted into the damaged disc space 70 in an inverted orientation and the process repeated to penetrate the endplate 76 of the second vertebra 74.

The multi-pronged awl may be used or adapted with a posterior or transforaminal approach for the spinal surgery or any other spinal surgical orientations or other surgical sites within the body.

In some embodiments, a method of repairing a damaged disc space between a first vertebra and a second vertebra neighboring the first vertebra includes determining the shape of the damaged disc space employing a radiographic method, such as, for example, by CT or DTS. In some embodiments, the radiographic method allow assessment of the shape of the damaged disc space, including the distance between the first vertebra and the second vertebra defining the damaged disc space, and the contour and the thickness of each opposing endplate within the disc space.

In some embodiments, the method further includes selecting a head portion of a multi-prong awl to have a predetermined height and/or contour based the distance between the first endplate and the second endplate and the contours of the first and second endplates.

In some embodiments, the method further includes selecting a plurality of prongs for the head portion based on the thickness of the first endplate. The selection may include the number of prongs, the length of the prongs, the sharpness of the prongs, or the configuration of the prongs in the head portion. The prongs are mounted in the head portion such that in an extended state, the prongs extend a predetermined distance into the first endplate with the back of the head portion positioned against the second endplate. In some embodiments, the predetermined distance is based on the determined thickness of the first endplate.

In some embodiments, the method also includes inserting the head of the multi-pronged awl in a retracted state into a space between the first vertebra and the second vertebra. In the retracted state, the prongs are retracted within a cavity of the head portion.

In some embodiments, the method further includes actuating a handle of the multi-pronged awl to move the prongs to an extended state past an edge of the cavity to contact and penetrate the predetermined distance into first endplate while the back surface of the head portion presses against the second endplate. In some embodiments, the head of the awl remains substantially stationary as the prongs penetrate the endplate. Once the prongs are subsequently retracted, the head of the awl may be repositioned to penetrate different areas of the intervertebral body space.

In some embodiments, the method further includes actuating the handle to return the prongs to the retracted state and withdrawing the head portion of the multi-pronged awl from the intervertebral body space. In some embodiments, radiographic images are taken to confirm appropriate placement and positioning of the instrument before the prongs are deployed. In some embodiments, subsequent radiographic images are taken to confirm appropriate penetration of the prongs after the prongs are deployed.

It will be appreciated that in some embodiments, surgical kits are provided that include a multi-pronged awl, including an array of shim inserts of various thicknesses for the multi-pronged awl, one or more of insertable elongate instruments for irrigation, lighting, visualization, and/or neuromonitoring. The kit may be provided based on one or more of size features of a patient or a patient anatomy.

All above-mentioned references are hereby incorporated by reference herein.

While the invention has been described with reference to one or more exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. In addition, all numerical values identified in the detailed description shall be interpreted as though the precise and approximate values are both expressly identified.

The invention claimed is:

1. A multi-pronged awl comprising:

a shaft portion having an axis along a length of the shaft portion;

a handle portion extending from a first end of the shaft portion;

a deployment shaft extending through the shaft portion and engaged at a proximal end with the handle portion, and having a distal end; and a head portion extending from the shaft portion at a second end of the shaft portion opposite the first end, the head portion comprising:

a housing having an interior cavity into which the distal end of the deployment shaft extends, the housing having opposing first and second sides, at least the first side having at least one through aperture;

a first trolley half and a second trolley half opposing one another in a direction orthogonal to the shaft portion axis and positioned within the housing, the first trolley half positioned adjacent an interior surface of the first side of the housing and the second trolley half positioned adjacent an interior surface of the second side of the housing, each of the first trolley half and the second trolley half including a plurality of threaded bores; and a plurality of prongs threadedly mounted to at least a portion of the threaded bores within at least the first trolley half;

wherein, in a retracted state, the first trolley half and the second trolley half are in contact with one another along at least a portion of their respective lengths and the plurality of prongs are wholly within the housing, and wherein activation of the handle portion moves the deployment shaft toward the second end of the shaft portion and between the first trolley half and the second trolley half to push the first trolley half and the second trolley half apart and toward the housing to thereby move the plurality of prongs orthogonal to the shaft portion axis and into an extended state wherein the plurality of prongs are extended through a single common aperture past an edge on the first side of the housing.

2. The multi-pronged awl of claim 1, wherein the shaft portion comprises a retainer shaft having a bore and an activation shaft extending into the bore of the retainer shaft along a central axis of the multi-pronged awl.

3. The multi-pronged awl of claim 2, wherein the handle portion comprises a handle knob and a retraction knob rotatably screwed into the handle knob along the central axis of the multi-pronged awl.

4. The multi-pronged awl of claim 1, wherein the head portion is contoured and sized to be received in an intervertebral body space.

5. The multi-pronged awl of claim 4, wherein the head portion further comprises a shim insert removably affixed to a second side of the housing to increase a height of the head portion.

6. A multi-pronged awl kit comprising:

a multi-pronged awl including:

a shaft portion having an axis along a length of the shaft portion;

a handle portion extending from a first end of the shaft portion;

a deployment shaft extending through the shaft portion and engaged at a proximal end with the handle portion, and having a distal end; and a head portion extending from the shaft portion at a second end of the shaft portion opposite the first end, the head portion comprising:

a housing having an interior cavity into which the distal end of the deployment shaft extends, the housing having opposing first and second sides, at least the first side having at least one through aperture;

a first trolley half and a second trolley half opposing one another in a direction orthogonal to the shaft portion axis and positioned within the housing, the first trolley half positioned adjacent an interior surface of the first side of the housing and the second trolley half positioned adjacent an interior surface of the second side of the housing, each of the first trolley half and the second trolley half including a plurality of threaded bores; and a plurality of prongs threadedly mounted to at least a portion of the threaded bores within at least the first trolley half;

wherein, in a retracted state, the first trolley half and the second trolley half are in contact with one another along at least a portion of their respective lengths and the plurality of prongs are wholly within the housing, and wherein activation of the handle portion moves the deployment shaft toward the second end of the shaft portion and between the first trolley half and the second trolley half to push the first trolley half and the second trolley half apart and toward the housing to thereby move the plurality of prongs orthogonal to the shaft portion axis and into an extended state wherein the plurality of prongs are extended through a single common aperture past an edge on the first side of the housing; and a plurality of interchangeable shim inserts having different thicknesses for affixing to a second side of the housing to adjust a height of the head portion.

7. A method of repairing a damaged disc space between a first vertebra and a second vertebra neighboring the first vertebra, the first vertebra and the second vertebra defining the damaged disc space, the method comprising:

actuating the handle of the multi-pronged awl of claim 1 to move the plurality of prongs orthogonal to the shaft portion axis of the multi-pronged awl from the retracted state within the interior cavity in the housing to the extended state extending through the single common aperture past the edge of the housing to contact and penetrate a predetermined distance into a first endplate of the first vertebra while a back surface of the head portion presses against a second endplate of the second vertebra.

8. The method of claim 7, further comprising, prior to the actuating, inserting the head portion of the multi-pronged awl into the damaged disc space.

9. The method of claim 7, further comprising, prior to the actuating, selecting the head portion of the multi-prong awl to have a predetermined height and a predetermined contour based on a distance between the first endplate and the second endplate, a contour of the first endplate, and a contour of the second endplate.

10. The method of claim 9, further comprising, prior to the selecting, determining the distance between the first endplate and the second endplate, the contour of the first endplate, the contour of the second endplate, and a thickness of the first endplate.

11. The method of claim 10, further comprising, prior to the selecting, mounting the prongs in the head portion such that in the extended state, the prongs extend a predetermined distance into the first endplate with the back of the head portion positioned against the second endplate based on the determined thickness of the first endplate.

12. The method of claim 7, further comprising, after the actuating, actuating the handle to return the prongs to the retracted state and withdrawing the head portion of the multi-pronged awl from the damaged disc space.

13. The method of claim 7, wherein the actuating does not crush the first endplate.

* * * * *